United States Patent [19]

Moody

[11] Patent Number: 4,958,697
[45] Date of Patent: Sep. 25, 1990

[54] ANATOMICALLY SHAPED EARSEALS FOR HEADSETS

[75] Inventor: Harold G. Moody, Hopedale, Mass.

[73] Assignee: The United States of America as represented by the Secretary of the Army, Washington, D.C.

[21] Appl. No.: 405,823

[22] Filed: Sep. 11, 1989

[51] Int. Cl.⁵ .......................... A42B 3/16; H04R 25/00
[52] U.S. Cl. ............................................ 181/129; 2/6;
2/423; 381/183; 381/187
[58] Field of Search .................... 181/129; 2/209, 5, 6,
2/423; 128/864, 866; 381/158, 183, 187

[56] References Cited

U.S. PATENT DOCUMENTS

| | | | |
|---|---|---|---|
| 1,368,307 | 2/1921 | Waldron | 181/129 |
| 2,856,469 | 10/1958 | Morse | 181/129 |
| 4,278,852 | 7/1981 | Gorike | 381/158 |
| 4,408,605 | 10/1983 | Doerr et al. | 128/864 X |
| 4,453,277 | 6/1984 | Durand et al. | 2/416 |
| 4,856,118 | 8/1989 | Sapiejewski | 2/209 |

Primary Examiner—Benjamin R. Fuller
Attorney, Agent, or Firm—Richard J. Donahue; Lawrence E. Labadini

[57] ABSTRACT

An anatomically shaped earseal is provided for headset earcups. The earseal is thinner at the top than at the bottom and gradually widens toward the bottom to evenly distribute the pressure and provide a tight seal with the wearer's head.

2 Claims, 1 Drawing Sheet

ANATOMICALLY SHAPED EARSEALS FOR HEADSETS

The invention described herein may be manufactured, used and licensed by or for the Government for Governmental purposes without the payment to me of any royalty thereon.

BACKGROUND OF THE INVENTION

This invention relates in general to sound attenuating earseals for use on communications and/or aural protective headset earcups and, more particularly, to anatomically shaped earseals for headsets.

Many of the communication headsets have a flat or nearly flat surface from which sound emanates. Normally, flanges are provided on the headsets to facilitate attachment to a flexible earseal which is often donut shaped and has a uniform surface in contact with the head of the wearer and uniform cross-sectional area. In many situations, such as when the user wears a helmet, hard hat, or sweatband, these conventional earseals may be highly compressed resulting in distortion of the shape of the flexible earseal and discomfort to the user. In many cases the distortion of the shape of the earseal caused by a helmet or hard hat results in a loss of sound attenuation.

SUMMARY OF THE INVENTION

A principle object of this invention is to provide an earseal for headset earcups which can be worn with comfort under a helmet or hard hat;

Another object of the invention is to provide an earseal for headset earcups which is compatible with a combat helmet;

Yet another object of the invention is to provide an earseal for headset earcups which is shaped to conform to the wearer's head when worn under a combat helmet.

Upon further study of the specification and appended claims, further objects and advantages of this invention will become apparent to those skilled in the art.

These objects are attained according to the invention by an anatomically shaped earseal which is generally donut shaped and has a non-uniform surface area and a non-uniform cross section. The earseal is adapted to receive a headset earcup having flat or nearly flat flanges. In a preferred embodiment, the earseal is formed of polyurethane foam with an outer layer of polyurethane film thereon. In another preferred embodiment, the cross-sectional area of the earseal varies as will be disclosed herein to be anatomically compatible with the head of a wearer and surface area varies in thickness around the circumference of the earseal to allow the earseal to more comfortably fit under a helmet or other head covering.

BRIEF DESCRIPTION OF FIGURES

The invention and further details of the invention will become more apparent from examples of embodiment presented hereinafter and illustrated schematically.

DETAILED DESCRIPTION

Figure 1:
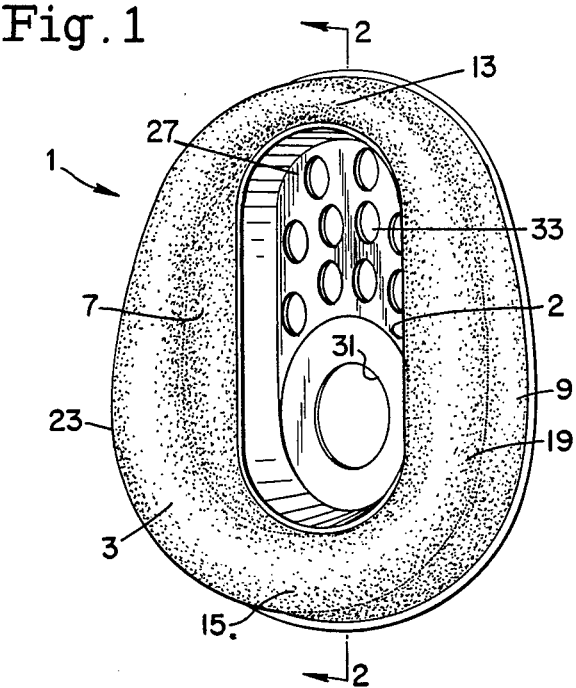
FIG. 1 is a perspective view of the earseals of the present invention.

FIG. 1 illustrates an earseal 1 which is donut shaped and defines an elliptical opening 2 adapted to receive an earphone (not shown). The earseal is defined by four surfaces, an inner facing surface 3 which bears against the head of the wearer, a flat outer facing surface 5 opposite to said inner facing surface which will be positioned against an earcup, an inner peripheral surface 7 defining the elliptical opening 2, and an outer surface 9 which defines the outer peripheral wall of the earseal.

Figure 2:
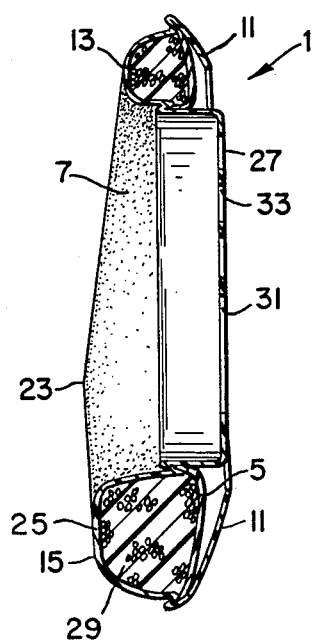
FIG. 2 shows the cross-sectional area of the earseal of FIG. 1 taken along the line 2—2.
Figure 3:
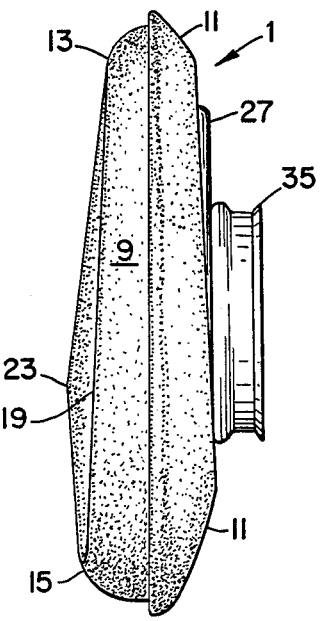
FIG. 3 is a side view of a left earseal illustrating the point of attachment of an earphone retainer.

As can be seen in FIGS. 1-3, and especially in the side views, the cross sectional thickness of the earseal from the outer facing surface 5 to the inner facing surface 3 varies so as to produce a variable outline or profile. In the embodiment best shown in FIG. 3 which represents the left earseal, the thickness of the earseal is constant from the top 13 to a point 19, and from point 19 to point 23 the thickness gradually increases, and from point 23 to the top 13 the thickness gradually decreases. Point 19 is approximately the point of intersection of an imaginary radial line drawn at 130 degrees from an imaginary center of the earseal. Point 23 approximates the point of intersection of an imaginary radial line drawn at 245 degrees from the same imaginary center. The contour obtained by varying the cross sectional thickness of the earseal from a flat outer facing surface 5 to produce the profile shown as the inner facing surface 3 in FIGS. 2 and 3 results in an earseal profile that fits or accomodates the anatomical contours about the ear of the wearer. The right earseal (not shown) would be the mirror image of the left earseal so that the thickest portion of the earseal would be at the imaginary 115 degree intersect and the constant thickness from the 230 degree intersect to the top of the earseal. In a preferred embodiment the thickness increases at a constant rate to the thickest point and decreases at the same constant rate to the thinnest point at 13. In one embodiment, the left earseal is 0.38 inch thick from point 13 to point 19 and increases by 0.002 inches for each degree to point 23 and then decreases by 0.002 for each degree from point 23 to point 13.

As shown in FIGS. 1 and 2, the width of the earseal measured from the inner peripheral surface 7 to the outer surface 9 is thinner at the top 13 than at the bottom 15. The width at the top is approximately ½ the width at the bottom, and the thin portion extends throughout the top half of the earseal and preferably throughout the top third of the earseal. This construction, with the earseal being thinner at the top than at the bottom, allows the earseal with earcup to more comfortably fit under a helmet or hard hat.

An integral flap 11 extends from the peripheral edge of the outer facing surface 5 around the earseal. This flap hooks over the flange of an earcup (not shown) to hold the earseal against an earcup.

A flexible diaphragm 27 is shown attached to the outer facing surface 5 of the earseal. The diaphragm is shown with an aperture 31 which is adapted to receive an electronic earphone (not shown) and a plurality of small openings 33 to allow non-electronic sounds to be transmitted to the ear. An earphone retainer 35 formed of a rigid material is attached to the diaphragm and holds an earphone in place.

The earseal of this invention may be constructed of any resilient material such as plastic and/or leather. In a preferred embodiment, the earseal is formed of foamed polyurethane 29 covered with an outer layer of polyurethane film 25.

The gradual widening of the earseals toward the bottom tends to cover a larger area, and this larger bearing surface more evenly distributes the pressure of an earcup against the wearer's head improving the comfort and sound attenuation of the earseals. The cross-sectional thickness also varies to form a more complete seal between the flat or nearly flat surface of the earcup flange and the anatomic shape of the side of the human head surrounding the ear.

The preceding examples can be repeated with similar success by substituting the generically or specifically described components of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

I claim:

1. An anatomically shaped resilient earseal for attachment to headset earcups with nearly flat flanges, said earseal being generally donut-shaped to define an elliptical opening, said earseal having a top, a bottom and an inner facing surface for contacting a head of a wearer of said earseal, said inner facing surface being thinner at said top than at said bottom, and having a variable cross section that creates an inwardly extending profile which matches an anatomical configuration of the head around an ear of the wearer, said elliptical opening containing a diaphragm having a plurality of holes therethrough for permitting externally produced sound to be transmitted through said diaphragm and having an earphone retainer attached about an aperture in said diaphragm.

2. The earseal of claim 1 wherein said plurality of holes in said diaphragm are positioned above said aperture and wherein said earphone retainer is formed of rigid material.

* * * * *